(12) United States Patent
Curtis

(10) Patent No.: US 10,124,152 B2
(45) Date of Patent: Nov. 13, 2018

(54) PERFUSION SYSTEM FOR TREATING CARDIAC RHYTHM DISTURBANCES

(71) Applicant: Guy P. Curtis, San Diego, CA (US)

(72) Inventor: Guy P. Curtis, San Diego, CA (US)

(73) Assignee: GUY P. CURTIS AND FRANCES L. CURTIS TRUST CA (US)

( * ) Notice: Subject to any disclaimer, the term of this patent is extended or adjusted under 35 U.S.C. 154(b) by 177 days.

(21) Appl. No.: 14/869,029

(22) Filed: Sep. 29, 2015

(65) Prior Publication Data
US 2017/0087342 A1   Mar. 30, 2017

(51) Int. Cl.
*A61M 25/10*   (2013.01)

(52) U.S. Cl.
CPC .. *A61M 25/1011* (2013.01); *A61M 25/10181* (2013.11); *A61M 2025/1015* (2013.01); *A61M 2025/1052* (2013.01); *A61M 2025/1097* (2013.01)

(58) Field of Classification Search
CPC ........ A61M 25/1011; A61M 25/10181; A61M 2025/1097; A61M 2025/1052; A61M 2025/1015
See application file for complete search history.

(56) References Cited

U.S. PATENT DOCUMENTS

| | | | |
|---|---|---|---|
| 6,416,493 B1* | 7/2002 | Del Giglio | A61M 25/1011 600/381 |
| 6,461,327 B1* | 10/2002 | Addis | A61M 25/1011 604/101.04 |
| 2002/0062125 A1* | 5/2002 | Altman | A61B 18/1492 606/41 |
| 2005/0015048 A1* | 1/2005 | Chiu | A61M 25/10 604/101.04 |
| 2012/0101476 A1* | 4/2012 | Curtis | A61M 25/0017 604/509 |

FOREIGN PATENT DOCUMENTS

WO   2002024248 A1   3/2002

OTHER PUBLICATIONS

PCT International Search Report, Application No. PCT/US2016/051543, dated Sep. 13, 2016.

* cited by examiner

*Primary Examiner* — Amber Stiles
(74) *Attorney, Agent, or Firm* — Nydegger & Associates

(57) ABSTRACT

A system and method for perfusing a liquid medicament into tissue of a patient requires a catheter having a distal barrier and a proximal barrier mounted on the catheter. A perfusion section is formed into the catheter between these barriers. By way of example of a typical operation, the catheter is advanced through the vasculature of a patient and into the coronary sinus. Advancement continues until the barriers of the catheter are positioned to straddle the ostium of the left atrial vein. As so positioned, a perfusion chamber is established in the coronary sinus between the barriers. Also, the perfusion chamber is positioned for fluid communication with the left atrial vein. Liquid medicament can then be transferred from a source into the perfusion chamber for perfusion of the medicament into tissue of the atrial vein.

13 Claims, 1 Drawing Sheet

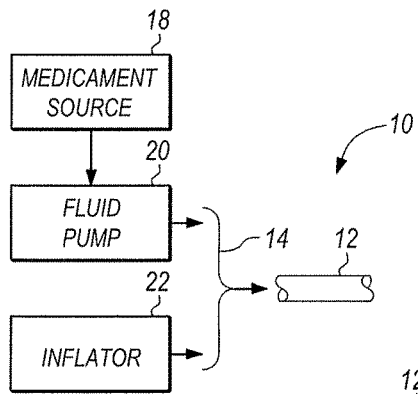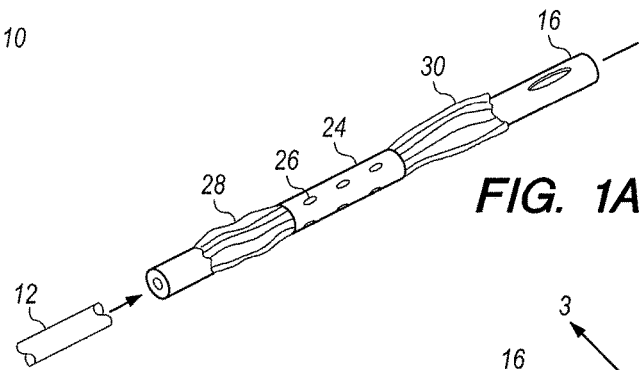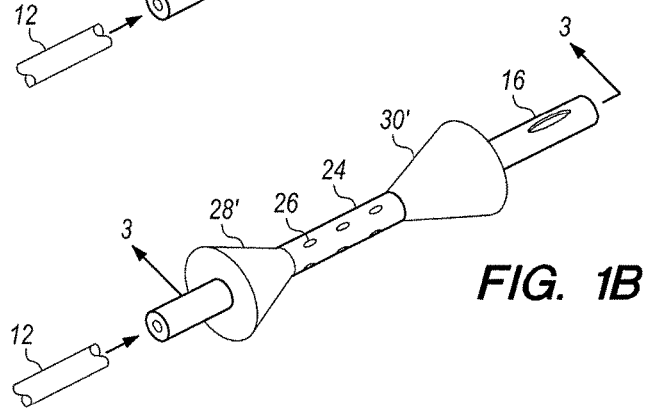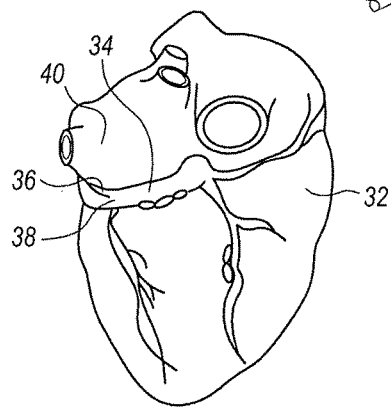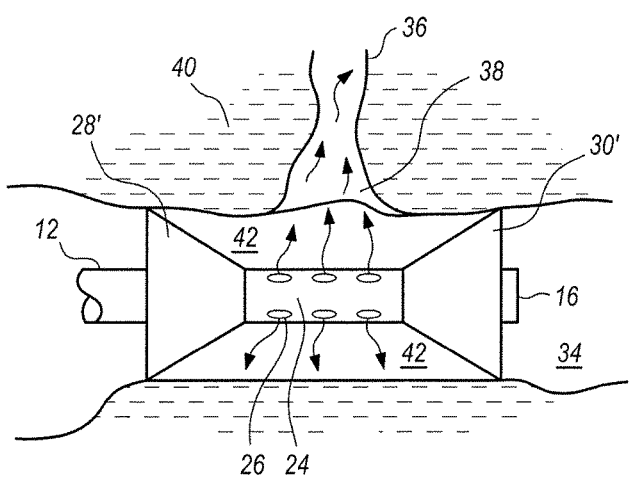

PERFUSION SYSTEM FOR TREATING CARDIAC RHYTHM DISTURBANCES

FIELD OF THE INVENTION

The present invention pertains generally to systems and methods for using catheters for therapeutic uses. More particularly, the present invention pertains to systems and methods for perfusing a liquid medicament into tissue of a patient. The present invention is particularly, but not exclusively, useful for establishing a perfusion chamber in the coronary sinus of a patient, for delivering a liquid medicament to the left atrial vein and a subsequent perfusion of the medicament into tissue of the left atrial vein.

BACKGROUND OF THE INVENTION

An effective drug delivery protocol for therapeutic purposes must necessarily be based on extensive evaluations of many diverse considerations. Of interest here, is the recognition that of the many different ways in which a drug can be delivered to a person, perfusion can be an effective methodology in many instances. Of particular interest, however, is the recognition that perfusion protocols can be efficacious for delivering medicaments to internal tissue.

For a perfusion protocol, the medicament will typically be a liquid, or a liquid-like substance, that will interact with a particular type of tissue, through a surface of the tissue. This requires the therapeutic component (i.e. drug) that is being used to have characteristics which will account for such operational variables as: 1) the required perfusion rate; 2) the necessary drug release rate; and 3) the preferred concentration gradient. All of this, of course, requires the use of a system or device which has the ability to deliver medicament to a specified site or location inside the body.

From an operational perspective, in order to implement an efficacious perfusion protocol it is obviously important to have a delivery system that will effectively interact with the anatomy of the patient. In overview, the general characteristics of such a delivery system will include capabilities that include: 1) accessing the perfusion site; 2) avoiding the disruption or impairment of physiological functions in the body during the conduct of a perfusion protocol; and 3) supporting an efficacious protocol for potentially prolonged periods of time.

As an example where a perfusion protocol for internal tissue may be effective, consider the condition of atrial fibrillation. It is known that atrial fibrillation, which is an involuntary contraction of an atrial in the heart muscle, can be treated in any of several different ways (e.g. using ablation techniques). It is also known, however, that atrial fibrillation can be treated pharmacologically. This latter case then leads to the consideration of a delivery system. For instance, consider U.S. patent application Ser. No. 14/275,583 filed on May 12, 2014, for an invention entitled "Catheter System for Venous Infusions" which is assigned to the same assignee as the present invention, and which is incorporated herein by reference.

With the above in mind, it is an object of the present invention to provide a delivery system and method having the ability to establish an effective and efficacious internal perfusion site in the body of a patient. Another object of the present invention is to provide a system and method for transferring a medicament to a selected location in the body of a patient for perfusion of the medicament into a tissue of the patient. Yet another object of the present invention is to provide a system and method for affecting the perfusion of a medicament into internal tissue of a patient that is easy to implement, is simple to operate and is comparatively cost effective.

SUMMARY OF THE INVENTION

In accordance with the present invention, a system and method for transferring a liquid medicament to a coronary sinus for subsequent perfusion into atrial tissue of a patient requires a perfusion catheter and a source of the medicament. Structurally, the perfusion catheter includes a perfusion section that is formed into the catheter between a proximal barrier and a distal barrier which are mounted on the catheter. Also included is a fluid pump for transferring the liquid medicament from an extracorporeal source of the medicament to the perfusion section of the catheter.

As envisioned for the present invention, both the proximal barrier and the distal barrier are, preferably, inflatable balloons. Accordingly, the system of the present invention will typically include an inflation pump that is connected in fluid communication with the distal barrier and with the proximal barrier for respectively inflating and deflating the barriers (balloons).

For an operation of the present invention, the perfusion catheter is advanced into position through the vasculature of the patient with both the proximal barrier and the distal barrier deflated. Specifically, advancement of the catheter continues until the distal barrier is positioned in the coronary sinus of the patient at a location that is distal to an ostium of an atrial vein (e.g. the left atrial vein). This advancement also positions the proximal barrier at a location that is proximal to the ostium of the atrial vein. Both barriers are then inflated. The result here is to establish a perfusion chamber in the coronary sinus between the proximal barrier and the distal barrier. Further consequences are that the perfusion section of the catheter is positioned in the perfusion chamber that is created, and the perfusion chamber is in fluid communication with the atrial vein through its ostium.

Once the catheter has been placed in the coronary sinus as indicated above, liquid medicament from the source of the medicament is transferred by the fluid pump to the perfusion section of the catheter. From there, the liquid medicament is introduced into the perfusion chamber. The liquid medicament then flows from the perfusion chamber and into the atrial vein for perfusion of the medicament into tissue of the atrium.

As envisioned for the present invention, the liquid medicament will have at least one predetermined pharmacological characteristic which is based on an operational capability of the medicament, such as a desired perfusion rate, a required drug release rate, or an effective concentration gradient. Depending on the needs of the particular perfusion protocol, another consideration for the present invention is that the medicament being used may be either a true liquid or a liquid-like substance. As an example of a liquid-like substance, the present invention envisions instances wherein it may be preferable for the therapeutic component of the medicament (i.e. the drug) to be carried on nano-particles.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a schematic-perspective view of a system in accordance with the present invention;

FIG. 1a shows the system in FIG. 1 with its proximal and distal barriers deflated for navigation through the vasculature of a patient;

FIG. 1b shows the system in FIG. 1 with its proximal and distal barriers inflated (deployed) for the conduct of a perfusion protocol in accordance with the present invention;

FIG. 2 is a view of a heart muscle showing the locations of the coronary sinus and the left atrial vein on the epicardial surface of the heart muscle; and FIG. 3 is an operational view of the perfusion section of the catheter system deployed with its associated distal and proximal barriers straddling the ostium of the left atrial vein, as would be seen along the line 3-3 in FIG. 1 (FIG. 1b).

DESCRIPTION OF THE PREFERRED EMBODIMENTS

Referring initially to FIG. 1, a system for transferring a liquid medicament to internal tissue of a patient in accordance with the present invention is shown and is generally designated 10. As shown, the system 10 includes a catheter 12 which has a proximal end 14 and a distal end 16 (FIGS. 1a and 1b). Also shown in FIG. 1 are extracorporeal components of the system 10 which include a medicament source 18 and a fluid pump 20 which is provided to transfer (pump) medicament from the source 18 into the catheter 12. As envisioned for the present invention, the medicament, when transferred from the source 18, may be either in a liquid form or in a liquid-like form. For instance, depending on the needs of an operational protocol for the system 10, it may happen that rather than being purely a liquid, the medicament being used may preferably be a liquid-like substance which includes a therapeutic component carried on nano-particles. FIG. 1 also shows that another extracorporeal component of the system 10 may be an inflator 22.

Still referring to FIG. 1, it will be seen in both FIGS. 1a and 1b that the catheter 12 is formed with a perfusion section 24 which is located proximal to the distal end 16 of the catheter 12. Also, it will be seen that the perfusion section 24 is formed with a plurality of holes, of which the hole 26 is exemplary. Further, FIG. 1 also shows that the catheter 12 includes both a proximal barrier 28 and a distal barrier 30, and that these barriers 28 and 30 together straddle the perfusion section 24. With regard to the barriers 28 and 30 it is to be noted that they are intended to alternate between two different configurations (i.e. FIG. 1a and FIG. 1b). In one configuration, FIG. 1a, the barriers 28 and 30 are shown deflated. For another configuration, FIG. 1b, the barriers 28' and 30' are shown inflated. In this context, it is implied that the proximal barrier 28 and the distal barrier 30 are preferably inflatable/deflatable devices, such as balloons.

Referring now to FIG. 2, it is to be appreciated that an intended environment for operation of the catheter 12 of the system 10 is the heart muscle 32. More particularly, the anatomical features of the heart muscle 32 which are of most interest here include the coronary sinus 34, the left atrial vein 36 and the ostium 38 of the left atrial vein 36. As indicated in several instances above, the present invention has been disclosed with reference to atrial fibrillation as an exemplary condition. Thus, to continue with this example, for a perfusion protocol with the treatment of atrial fibrillation as its objective, the internal tissue of interest for the perfusion protocol will be the atrium 40.

In an operation of the present invention, the catheter 12 of the system 10 is advanced through the vasculature of a patient (not shown) until the perfusion section 24 of the catheter 12 is positioned in the coronary sinus 34. In particular, this position will be substantially adjacent the ostium 38 of the atrial vein 36. During this advancement, both the proximal barrier 28 and the distal barrier 30 are withdrawn or deflated as shown in FIG. 1a. However, once the perfusion section 24 has been properly positioned in the coronary sinus 34, the inflator 22 is activated to inflate (deploy) the proximal barrier 28' and the distal barrier 30'. As best seen with reference to FIG. 3, with a deployment of the proximal barrier 28' and the distal barrier 30', a perfusion chamber 42 is created. Importantly, the perfusion chamber 42 is established so it will be in fluid communication with the atrial vein 36, via the ostium 38 of the atrial vein 36.

With the perfusion section 24 in position as disclosed above, and as shown in FIG. 3, the fluid pump 20 is activated to transfer medicament from the medicament source 18 to the catheter 12, and to the perfusion section 24 of the catheter 12. At the perfusion section 24, medicament exits from the perfusion section 24 through the plurality of holes 26 and into the perfusion chamber 42. From the perfusion chamber 42, the medicament enters the atrial vein 36 through its ostium 38 as shown in FIG. 3. As intended for the present invention, the medicament will then perfuse from the atrial vein 36 and into tissue of the atrium 40.

As mentioned above, several factors require specific considerations for the conduct of a perfusion protocol. In each instance, however, a perfusion protocol in accordance with the present invention will necessarily include the proper placement of a catheter 12, along with the creation of a perfusion chamber 42 from which a medicament can be perfused. Further, after each perfusion protocol has been completed, the barriers 28 and 30 are to be deflated, and the catheter 12 withdrawn from the vasculature.

While the particular Perfusion System for Treating Cardiac Rhythm Disturbances as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for transferring a medicament to a perfusion chamber in a coronary sinus for subsequent perfusion into atrial tissue from an atrial vein of a patient which comprises:

a source of the medicament;

a perfusion catheter having a distal end and a proximal end;

a distal barrier mounted on the perfusion catheter, wherein the distal barrier is to be positioned in contact with the coronary sinus at a location distal and adjacent to an ostium of the atrial vein;

a proximal barrier mounted on the perfusion catheter, wherein the proximal barrier is to be positioned in contact with the coronary sinus at a location proximal and adjacent to the ostium of the atrial vein, wherein the proximal barrier and the distal barrier straddle the ostium of the atrial vein to establish and confine the perfusion chamber between the proximal barrier and the distal barrier in the coronary sinus for direct fluid communication with the atrial vein, and wherein the perfusion chamber is continuously maintained in accordance with an efficacious protocol for a prolonged period of time;

a perfusion section formed into the catheter between the proximal barrier and the distal barrier; and a fluid pump for transferring the medicament from the source to the perfusion section of the catheter, and from the catheter into the perfusion chamber for an uninterrupted perfusion of the medicament in the atrial vein.

2. The system recited in claim 1 wherein the medicament is a liquid.

3. The system recited in claim 1 wherein the medicament is carried on nano-particles.

4. The system recited in claim 1 wherein the medicament has at least one predetermined pharmacological characteristic.

5. The system recited in claim 4 wherein the pharmacological characteristic is based on an action capability of the medicament and is selected from the group consisting of a perfusion rate, a release rate, and a concentration gradient.

6. The system recited in claim 1 wherein the distal barrier and the proximal barrier are each an inflatable balloon.

7. The system recited in claim 6 further comprising an inflation pump connected in fluid communication with the distal barrier and with the proximal barrier for respectively inflating and deflating the balloons.

8. A method for transferring a medicament to a perfusion chamber in a coronary sinus for perfusion into atrial tissue from an atrial vein of a patient which comprises the steps of:

providing a perfusion catheter having a distal end and a proximal end, with a distal barrier and a proximal barrier respectively mounted on the perfusion catheter with a perfusion section formed into the perfusion catheter between the proximal barrier and the distal barrier;

advancing the perfusion catheter through the vasculature of the patient to position the distal barrier in contact with the coronary sinus at a location distal and adjacent to an ostium of the atrial vein and to position the proximal barrier in contact with the coronary sinus at a location proximal and adjacent to the ostium of the atrial vein, wherein the proximal barrier and the distal barrier straddle the ostium of the atrial vein to establish and confine the perfusion chamber between the proximal barrier and the distal barrier in the coronary sinus, and wherein the perfusion chamber is continuously maintained in accordance with an efficacious protocol for a prolonged period of time; and transferring the medicament from a source of the medicament to the perfusion section of the catheter and from the catheter into the perfusion chamber for an uninterrupted direct perfusion of the medicament in the atrial vein.

9. The method recited in claim 8 further comprising the step of selecting the medicament based on at least one predetermined pharmacological characteristic.

10. The method recited in claim 9 wherein the selecting step is accomplished based on an action capability of the medicament selected from the group consisting of a perfusion rate, a release rate, and a concentration gradient.

11. The method recited in claim 8 wherein the distal barrier and the proximal barrier are each an inflatable balloon, and the method further comprises the step of respectively inflating and deflating the balloons to selectively establish the perfusion chamber in the coronary sinus.

12. The method recited in claim 8 wherein the medicament is a liquid.

13. The method recited in claim 8 wherein the medicament is carried on nano-particles.

* * * * *